(12) United States Patent  
Kim et al.

(10) Patent No.: US 8,182,835 B2  
(45) Date of Patent: *May 22, 2012

(54) SUSTAINED-RELEASE LIPOSOMAL ANESTHETIC COMPOSITIONS

(75) Inventors: Sinil Kim, Solana Beach, CA (US); Taehee Kim, Los Angeles, CA (US); Sharad Murdande, Groton, CT (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/097,756

(22) Filed: Apr. 1, 2005

(65) Prior Publication Data

US 2006/0078606 A1  Apr. 13, 2006

Related U.S. Application Data

(63) Continuation of application No. PCT/US98/19583, filed on Sep. 18, 1998.

(60) Provisional application No. 60/059,233, filed on Sep. 18, 1997.

(51) Int. Cl.  
*A61K 9/127* (2006.01)

(52) U.S. Cl. ............ 424/450; 364/4.1; 364/4.3; 364/4.6

(58) Field of Classification Search .................. 424/450; 264/4.1, 4.3, 4.6  
See application file for complete search history.

(56) References Cited

U.S. PATENT DOCUMENTS

| | | |
|---|---|---|
| 3,684,251 A | 8/1972 | Bowling |
| 3,946,994 A | 3/1976 | Mertz et al. |
| 4,026,817 A | 5/1977 | Ciuti et al. |
| 4,078,052 A | 3/1978 | Papahadjopoulos |
| 4,089,801 A | 5/1978 | Schneider |
| 4,113,765 A | 9/1978 | Richardson et al. |
| 4,145,410 A | 3/1979 | Sears |
| 4,224,179 A | 9/1980 | Schneider |
| 4,235,587 A | 11/1980 | Miles |
| 4,235,871 A | 11/1980 | Papahadjopoulos et al. |

(Continued)

FOREIGN PATENT DOCUMENTS

CA 2078666 9/1991

(Continued)

OTHER PUBLICATIONS

Assil et al., "Liposome Suppression of Proliferative Vitreoretinopathy: Rabbit Model Using Antimetabolite Encapsulated Liposomes," Invest. Ophthalmol. Vis. Sci., 32(11):2891-2897, 1991.

(Continued)

*Primary Examiner* — Gollamudi Kishore  
(74) *Attorney, Agent, or Firm* — Knobbe Martens Olson & Bear LLP

(57) ABSTRACT

The invention provides a method for obtaining local anesthetics encapsulated in liposomes, such as multivesicular liposomes, with high encapsulation efficiency and slow release in vivo. When the encapsulated anesthetic is administered as a single intracutaneous dose, the duration of anesthesia and half-life of the drug at the local injection site is increased as compared to injection of unencapsulated anesthetic. The maximum tolerated dose of the encapsulated anesthetic is also markedly increased in the liposomal formulation over injection of unencapsulated anesthetic. These results show that the liposomal formulation of local anesthetic is useful for sustained local infiltration and nerve block anesthesia.

21 Claims, 3 Drawing Sheets

U.S. PATENT DOCUMENTS

| | | | |
|---|---|---|---|
| 4,310,506 A | 1/1982 | Baldeschwieler et al. | |
| 4,394,372 A | 7/1983 | Taylor | |
| 4,454,083 A | 6/1984 | Brown et al. | |
| 4,478,824 A | 10/1984 | Franco et al. | |
| 4,522,803 A | 6/1985 | Lenk et al. | |
| 4,588,578 A | 5/1986 | Fountain et al. | |
| 4,590,030 A | 5/1986 | Gillner et al. | |
| 4,599,227 A | 7/1986 | Dees et al. | |
| 4,599,342 A | 7/1986 | LaHann | |
| 4,610,868 A | 9/1986 | Fountain et al. | |
| 4,622,219 A | 11/1986 | Haynes | |
| 4,668,580 A | 5/1987 | Dahm et al. | |
| 4,711,782 A | 12/1987 | Okada et al. | |
| 4,725,442 A | 2/1988 | Haynes | |
| 4,744,989 A | 5/1988 | Payne et al. | |
| 4,752,425 A | 6/1988 | Martin et al. | |
| 4,761,255 A | 8/1988 | Dahm et al. | |
| 4,761,288 A | 8/1988 | Mezei | |
| 4,769,250 A | 9/1988 | Forssen | |
| 4,776,991 A | 10/1988 | Farmer et al. | |
| 4,781,871 A | 11/1988 | West, III et al. | |
| 4,844,620 A | 7/1989 | Lissant et al. | |
| 4,844,904 A | 7/1989 | Hamaguchi et al. | |
| 4,861,597 A | 8/1989 | Kida et al. | |
| 4,877,561 A | 10/1989 | Iga et al. | |
| 4,877,619 A | 10/1989 | Richer | |
| 4,908,463 A | 3/1990 | Bottelberghe | |
| 4,920,016 A | 4/1990 | Allen et al. | |
| 4,921,644 A | 5/1990 | Lau et al. | |
| 4,921,853 A | 5/1990 | LeBlanc | |
| 4,937,078 A | 6/1990 | Mezei et al. | |
| 4,946,683 A | 8/1990 | Forssen | |
| 5,000,959 A | 3/1991 | Iga et al. | |
| 5,004,611 A | 4/1991 | Leigh | |
| 5,013,556 A | 5/1991 | Woodle et al. | |
| 5,019,394 A | 5/1991 | Hamaguchi et al. | |
| 5,021,200 A | 6/1991 | Vanlerberghe et al. | |
| 5,049,392 A | 9/1991 | Weiner et al. | |
| 5,077,056 A | 12/1991 | Bally et al. | |
| 5,091,187 A | 2/1992 | Haynes | |
| 5,094,854 A | 3/1992 | Ogawa et al. | |
| 5,141,674 A | 8/1992 | Leigh | |
| 5,147,134 A | 9/1992 | Bradley et al. | |
| 5,169,637 A | 12/1992 | Lenk et al. | |
| 5,186,941 A | 2/1993 | Callahan et al. | |
| 5,192,549 A | 3/1993 | Barenolz et al. | |
| 5,204,112 A | 4/1993 | Hope et al. | |
| 5,211,955 A | 5/1993 | Legros et al. | |
| 5,225,212 A | 7/1993 | Martin et al. | |
| 5,227,165 A | 7/1993 | Domb et al. | |
| 5,227,170 A | 7/1993 | Sullivan | |
| 5,244,678 A * | 9/1993 | Legros et al. | 424/450 |
| 5,246,707 A | 9/1993 | Haynes | |
| 5,261,903 A | 11/1993 | Dhaliwal et al. | |
| 5,321,012 A | 6/1994 | Mayer et al. | |
| 5,334,381 A | 8/1994 | Unger | |
| 5,334,391 A | 8/1994 | Clark et al. | |
| 5,364,632 A | 11/1994 | Benita et al. | |
| 5,393,530 A | 2/1995 | Schneider et al. | |
| 5,407,660 A | 4/1995 | Bosworth et al. | |
| 5,422,120 A | 6/1995 | Kim | |
| 5,451,408 A | 9/1995 | Mezei et al. | |
| 5,455,044 A | 10/1995 | Kim et al. | |
| RE35,192 E | 3/1996 | Reese | |
| 5,543,158 A | 8/1996 | Gref et al. | |
| 5,576,017 A | 11/1996 | Kim | |
| 5,576,018 A | 11/1996 | Kim et al. | |
| 5,589,189 A | 12/1996 | Moynihan | |
| 5,635,205 A | 6/1997 | Nyqvist et al. | |
| 5,662,931 A | 9/1997 | Munechika et al. | |
| 5,700,482 A | 12/1997 | Frederiksen et al. | |
| 5,708,011 A | 1/1998 | Bardsley et al. | |
| 5,723,147 A | 3/1998 | Kim et al. | |
| 5,766,627 A * | 6/1998 | Sankaram | 424/450 |
| 5,770,222 A | 6/1998 | Unger et al. | |
| 5,776,486 A | 7/1998 | Castor et al. | |
| 5,807,573 A | 9/1998 | Ljusberg-Wahren et al. | |
| 5,814,335 A | 9/1998 | Webb et al. | |
| 5,827,533 A | 10/1998 | Needham | |
| 5,837,282 A | 11/1998 | Fenske et al. | |
| 5,849,763 A | 12/1998 | Bardsley et al. | |
| 5,853,755 A | 12/1998 | Foldvari | |
| 5,865,184 A | 2/1999 | Takiguchi | |
| 5,882,679 A | 3/1999 | Needham | |
| 5,885,260 A | 3/1999 | Mehl, Sr. et al. | |
| 5,891,467 A | 4/1999 | Willis | |
| 5,891,842 A | 4/1999 | Kream | |
| 5,895,661 A | 4/1999 | Tournier et al. | |
| 5,912,271 A | 6/1999 | Brodin et al. | |
| 5,922,340 A | 7/1999 | Berde et al. | |
| 5,942,253 A | 8/1999 | Gombotz et al. | |
| 5,948,441 A | 9/1999 | Lenk et al. | |
| 5,955,479 A | 9/1999 | Bardsley et al. | |
| 5,962,016 A | 10/1999 | Willis | |
| 5,962,532 A | 10/1999 | Campbell et al. | |
| 5,977,326 A | 11/1999 | Scheinmann et al. | |
| 5,980,927 A | 11/1999 | Nelson et al. | |
| 5,997,899 A | 12/1999 | Ye et al. | |
| 6,045,824 A * | 4/2000 | Kim et al. | 424/450 |
| 6,046,187 A | 4/2000 | Berde et al. | |
| 6,048,545 A * | 4/2000 | Keller et al. | 424/450 |
| 6,066,331 A | 5/2000 | Barenholz et al. | |
| 6,103,741 A | 8/2000 | Bardsley et al. | |
| 6,106,858 A | 8/2000 | Ye et al. | |
| 6,120,797 A | 9/2000 | Meers et al. | |
| 6,132,766 A * | 10/2000 | Sankaram et al. | 424/450 |
| 6,171,613 B1 | 1/2001 | Ye et al. | |
| 6,193,998 B1 | 2/2001 | Ye et al. | |
| 6,221,401 B1 | 4/2001 | Zasadzinski et al. | |
| 6,238,702 B1 | 5/2001 | Berde et al. | |
| 6,241,999 B1 | 6/2001 | Ye et al. | |
| 6,306,432 B1 | 10/2001 | Shirley et al. | |
| 6,399,094 B1 | 6/2002 | Brandl et al. | |
| 6,417,201 B1 | 7/2002 | Bardsley et al. | |
| 2002/0041895 A1 | 4/2002 | Gregoriadis et al. | |

FOREIGN PATENT DOCUMENTS

| | | |
|---|---|---|
| CA | 1323568 | 10/1993 |
| CA | 1337273 | 10/1995 |
| CA | 2176712 | 3/1996 |
| CA | 2199004 | 3/1996 |
| EP | 0 126 580 | 11/1984 |
| EP | 0 506 639 | 9/1992 |
| EP | 0280503 B1 | 7/1993 |
| GB | 2050287 | 1/1981 |
| JP | 61-27918 | 2/1986 |
| WO | WO 89/00846 | 2/1989 |
| WO | WO 89/04656 | 6/1989 |
| WO | WO 91/14445 | 10/1991 |
| WO | WO 93/00888 | 1/1993 |
| WO | WO 94/08565 A | 4/1994 |
| WO | WO 94/08626 | 4/1994 |
| WO | WO 94/22430 | 10/1994 |
| WO | WO 94/23697 | 10/1994 |
| WO | WO 94/26250 | 11/1994 |
| WO | WO 94/26253 A | 11/1994 |
| WO | WO 94/27581 | 12/1994 |
| WO | WO 95/13796 | 5/1995 |
| WO | WO 96/08235 | 3/1996 |
| WO | WO 96/14057 | 5/1996 |
| WO | WO 97/03652 | 6/1997 |

OTHER PUBLICATIONS

Assil et al., "Multivesicular Liposomes: Sustained Release of the Antimetabolite Cytarabine in the Eye," Arch Ophthalmol., 105(3):400-403, 1987.

Assil et al., "Tobramycin Liposomes: Single Subconjunctival Therapy of Pseudomonal Keratitis," Invest. Ophthalmol. Vis. Sci., 32(13):3216-3220, 1991.

Bonetti et al., "An extended-release formulation of methotrexate for subcutaneous administration,"Cancer Chemother. Pharmacol., 33:303-306, 1994.

Chamberlain et al., "Treatment of Leptomeningeal Metastasis With Intraventricular Administration of Depot Cytarabine (DTC 101): A Phase I Study," Arch. Neurol., 50:261-264, 1993.

Chatelut et al., "A slow-release methotrexate formulation for intrathecal chemotherapy," Cancer Chemother. Pharmacol., 32:179-182, 1993.

Kim "Liposomes as Carriers of Cancer Chemotherapy: Current status and Future Prospects," Drugs, 46(4):618-638,1993.

Kim et al., "Direct Cerebrospinal Fluid Delivery of an Antiretroviral Agent Using Multivesicular Liposomes," J. Infect. Dis., 162(3):750-752, 1990.

Kim et al., "Multivesicular Liposomes Containing 1-beta-D-Arabinofuranosylcytosine for Slow-Release Intrathecal Therapy," Cancer Res., 47(15):3935-3937, 1987.

Kim et al., "Multivesicular Liposomes Containing Cytarabine Entrapped in the Presence of Hydrochloric Acid for Intracavitary Chemotherapy," Cancer Treat. Rep., 71(7-8):705-711, 1987.

Kim et al., "Multivesicular Liposomes Containing Cytarabine for Slow-Release Sc Administration," Cancer Treat. Rep., 71(5):447-450, 1987.

Kim et al., "Preparation of Multivesicular Liposomes," Biochim. Biophys. Acta, 728(3):339-348, 1983.

Kim et al., "Prolongation of Drug Exposure in Cerebrospinal Fluid by Encapsulation into DepoFoam," Cancer Res., 53(7):1596-1598, 1993.

Roy et al., "Multivesicular liposomes containing bleomycin for subcutaneous administration," Cancer Chemother. Pharmacol., 28(2):105-108, 1991.

Shakiba et al., "Evaluation of Retinal Toxicity and Liposome Encapsulation of the Anti-CMV drug 2'-nor-cyclic GMP," Invest. Ophthalmol. Vis. Sci., 34(10):2903-2910, 1993.

Skuta et al., "Filtering Surgery in Owl Monkeys Treated with the Antimetabolite 5-Fluorouridine 5' Monophosphate Entrapped in Multivesicular Liposomes," Am. J. Ophtmalmol., 103(5):714-716, 1987.

Turski et al., "Magnetic Resonance Imaging of Rabbit Brain after Intracarotid Injection of Large Multivesicular Liposomes Containing Paramagnetic Metals and DTPA," Magn. Reson. Med., 7(2):184-196, 1998.

Kim et al., "Extended-release formulation of morphine for subcutaneous administration," *Cancer Chemother. Pharmacol.*, 1993, 33(3):187-190.

Kim et al., "Extended CSF Cytarabine Exposure Following Intrathecal Administration of DTC 101," *J. Olin. Oncol.*, 1993, 11(11):2186-2193.

Canadian Office Action mailed on May 16, 2002 in Canadian Patent Application No. 2,304,096, filed Sep. 18, 1998.

European Office Action mailed on Jan. 28, 2008 in European Patent Application No. 98 948 352.4, filed Sep. 18, 1998.

European Office Action mailed on May 8, 2007 in European Patent Application No. 98 948 352.4, filed Sep. 18, 1998.

Supplementary European Search Report dated Apr. 3, 2006 in European Patent Application No. 98 948 352.4, filed Sep. 18, 1998.

Norwegian Office Action mailed Jan. 26, 2010 in Norwegian Patent Application No. 2000 1410, with a filing date of Sep. 18, 1998.

Japanese Office Action mailed on Jan. 13, 2009 in Japanese Patent Application No. 2000-511489, filed on Sep. 18, 1998.

International Search Report mailed on Dec. 22, 1998 in PCT Application No. PCT/US98/19583, filed Sep. 18, 1998.

Written Opinion mailed on Jul. 13, 1999 in PCT Application No. PCT/US98/19583, filed Sep. 18, 1998.

International Preliminary Examination Report mailed on Jun. 29, 2000 in PCT Application No. PCT/US98/19583, filed Sep. 18, 1998.

Andrews et al., "Boundary Layer Solution for a Bubble Rising Through a Liquid Containing Surface-Active Contaminants," *Ind. Eng. Chem. Res.*, 1995, 34(4):1371-1382.

Arroyo et al., "Use of intermittent jets to enhance flux in crossflow filtration," *J. Membrane Sci.*, 1993, 80:117-129.

Bangham et al., "Diffusion of Univalent Ions Across the Lamellae of Swollen Phospholipids," *J. Mol. Biol.*, 1965, 13:238-252.

Barbet et al., "Weak acid-induced release of liposome-encapsulated carboxyfluorescein," *Biochim. Biophys. Acta*, 1984, 772:347-356.

Chattopadhyay et al., "The Protective Effect of Specific Medium Additives with Respect to Bubble Rupture," *Biotechnol. Bioeng.*, 1995, 45(6):473-480.

Chemical Comprehensive Dictionary, compact $2^{nd}$ ed., Kyoritsushuppan Corp., edited by the Editorial Committee of the Chemical Comprehensive Dictionary, Aug. 25, 1963, pp. 725-726.

Cherry et al., "Cell Death in the Thin Films of Bursting Bubbles," *Biotechnol. Prog.*, 1992, 8(1):11-18.

Cullis et al., "Structural Properties and Functional Roles of Phospholipids in Biological Membranes," Phospholipids and Cellular Regulation, pp. 1-59, vol. 1, J.F. Kuo ed., CRC Press, 1985, Boca Raton, FL.

Edwards et al., "Large Porous Particles for Pulmonary Drug Delivery," *Science*, 1997, 276: 1868-1871.

Frucht-Perry et al., "Fibrin-Enmeshed Tobramycin Liposomes: Single Application Topical Therapy of *Pseudomonas* Keratitis," *Cornea*, 1992, 11(5):393-397.

Gruner et al., "Novel Multilayered Lipid Vesicles: Comparison of Physical Characteristics of Multilamellar Liposomes and Stable Plurilamellar Vesicles," *Biochemistry*, 1985, 24(12):2833-2842.

Holdich et al., "The variation of crossflow filtration rate with wall shear stress and the effect of deposit thickness," *Chemical Engineering Research and Design (Trans IChem)*, 1995, 73(part A):20-26.

Huang, "Studies on Phosphatidylcholine Vesicles. Formation and Physical Characteristics," *Biochemistry*, 1969, 8(1):344-352.

Ishii, "Production and size control of large unilamellar liposomes by emulsification," Liposome Technology $2^{nd}$ Edition, pp. 111-121, vol. 1, Gregory Gregoriadis ed., CRC Press, 1993, Boca Raton, FL.

Jaffrin et al., "Energy saving pulsatile mode cross flow filtration," *J. Membrane Sci.*, 1994, 86:281-290.

Johnson et al., "New nozzle improves FCC feed atomization, unit yield patterns," *Oil and Gas Journal*, 1994, 92(3):80-86.

Kawashima et al., "Shear-Induced Phase Inversion and Size Control of Water/Oil/Water Emulsion Droplets with Porous Membrane," *J. Colloid Interface Sci.*, 1991, 145(2):512-523.

Kim et al., "Preparation of cell-size unilamellar liposomes with high captured volume and defined size distribution," *Biochim. Biophys. Acta*, 1981, 646:1-9.

Kim et al., "Preparation of multilamellar vesicles of defined size-distribution by solvent-spherule evaporation," *Biochim. Biophys. Acta*, 1985, 812:793-801.

Kim et al., "Modulation of the peritoneal clearance of liposomal cytosine arabinoside by blank liposomes," *Cancer Chemother. Pharmacol.*, 1987, 19(4):307-310.

Maa et al., "Liquid-liquid emulsification by rotor/stator homogenization," *J. Controlled Release*, 1996, 38:219-228.

Maestre et al, "Contribution of Light Scattering to the Circular Dichroism of Deoxyribonucleic Acid Films, Deoxyribonucleic Acid-Polylysine Complexes, and Deoxyribonucleic Acid Particles in Ethanolic Buffers," *Biochemistry*, 1980, 19(23): 5214-5223.

Mancini "Mastering the mix: Why Leave Mixing to Chance? Get a Proper Mix and a Better Product Every Time," *Food Engineering*, Mar. 1996, pp. 79-83.

Maranges et al., "Crossflow Filtration of *Saccharomyces cerevisiae* Using an Unsteady Jet," *Biotechnol. Tech.*, 1995, 9(9): 649-654.

Matsumoto et al., "An Attempt at Preparing Water-in-Oil-in-Water Multiple-Phase Emulsions," *J. Colloid Interface Sci.*, 1976, 57(2):353-361.

Michaels et al., "Sparging and Agitation-Induced Injury of Cultured Animal Cells: Do Cell-to-Bubble Interactions in the Bulk Liquid Injure Cells?" *Biotechnol. Bioeng.*, 1996, 51(4):399-409.

Mutsakis et al., "Advances in Static Mixing Technology," *Chem. Eng. Prog*, Jul. 1986, pp. 42-48.

Narhi et al., "Role of Native Disulfide Bonds in the Structure and Activity of Insulin-like Growth Factor 1: Genetic Models of Protein-Folding Intermediates," *Biochemistry*, 1993, 32(19):5214-5221.

Paul, "Reaction Systems for Bulk Pharmaceutical Production," *Chem. Ind.*, May 21, 1990, pp. 320-325.

Redkar et al., "Cross-Flow Microfiltration with High-Frequency Reverse Filtration," *AIChE Journal*, 1995, 41(3):501-508.

Rodgers et al., "Reduction of Membrane Fouling in the Ultrafiltration of Binary Protein Mixtures," *AIChE Journal*, 1991, 37(10):1517-1528.

Russack et al., "Quantitative Cerebrospinal Fluid Cytology in Patients Receiving Intracavitary Chemotherapy," *Ann. Neurol.*, 1993, 34(1):108-112.

Saberi et al., "Bubble Size and Velocity Measurement in Gas-Liquid Systems: Application of Fiber Optic Technique to Pilot Plant Scale," *Can. J. Chem. Eng.*, 1995, 73: 253-257.

Streiff et al., "Don't overlook static-mixer reactors," *Chem. Eng.*, Jun. 1994, pp. 76-82.

Szoka et al., "Comparative properties and methods of preparation of lipid vesicles (liposomes)," *Ann. Rev. Biophys. Bioeng.*, 1980, 9:467-508.

"Local Anesthetics," New Pharmacology, Revised $3^{rd}$ ed., pp. 261-266, Tanaka et al. eds. Nankoudou Corp., Aug. 1, 1997.

Tanaka et al., "Crossflow Filtration of Baker's Yeast with Periodical Stopping of Permeation Flow and Bubbling," *Biotechnol. Bioeng.*, 1995, 47(3):401-404.

Tsuchiya et al., "Tortuosity of Bubble Rise Path in a Liquid-Solid Fluidized Bed: Effect of Particle Shape," *AIChE Journal*, 1995, 41(6):1368-1374.

Watts et al., "Microencapsulation Using Emulsification/Solvent Evaporation: An Overview of Techniques and Applications," Critical Reviews in Therapeutic Drug Carrier Systems, 1990, 7(3):235-259.

Boogaerts et al. "Plasma concentrations of bupivacaine after brachial plexus administration of liposome-associated and plain solutions to rabbits," *Can. J. Anaesth*, 1993, 40:1201-1204.

Boogaerts et al. "Toxicity of Bupivacaine Encapsulated into Liposomes and Injected Intravenously: Comparison with Plan Solutions," *Anesth. Analg.*, 1993, 76:553-555.

Boogaerts et al. "Epidural Administration of Liposome-Associated Bupivacaine for the Management of Postsurgical Pain: A First Study," *J. Clin. Anesth*, 1994, 6:315-320.

Boogaerts et al. "Biodistribution of liposome-associated bupivacaine after extradural administration to rabbits," *Br. J. Anaesth*, 1995, 75:319-325.

Boogaerts et al. "Motor Blockade and Absence of Local Nerve Toxicity Induced by Liposomal Bupivacaine Injected into the Axillary Plexus of Rabbits," *Acta Anesth. Belg.*, 1995, 46:19-24.

Lafont et al. "Use of Liposome-Associated Bupivacaine for the Management of a Chronic Pain Syndrome," *Anesth. Analg.*, 1994, 79:818.

Lafont et al. "Use of Liposome-Associated Bupivacaine in a Cancer Pain Syndrome," *Anaesthesia* 1996, 51:578-579.

Legros et al. "Influence of Different Liposomal Formulations on the Pharmacokinetics of Encapsulated Bupivacain," [Abstract]. *Anesthesiology*, 1990, 73:A851.

Malinovsky et al. "Neurotoxilogical Assessment After Intracisternal Injection of Liposomal Bupivacaine in Rabbits," *Anesth. Analg.*, 1997, 85:1331-1336.

Mashimo et al. "Prolongation of Canine Epidural Anesthesia by Liposome Encapsulation of Lidocaine," *Anesth. Analg.*, 1992, 74:827-834.

Kim, T. et al., "Extended-release formulations of morphine for subcutaneous administration," Cancer Chemother. Pharmacol., vol. 33, pp. 187-190 (1993).

\* cited by examiner

SUSTAINED-RELEASE LIPOSOMAL ANESTHETIC COMPOSITIONS

This is a continuation of International Application Serial Number PCT/US98/19583, with an international filing date of Sep. 18, 1998, published in English under PCT Article 21(2) (now abandoned), which claims priority to U.S. Provisional Application Serial Number 60/059,233, filed on Sep. 18, 1997 is (now expired), both of which are incorporated by reference herein in their entirety.

BACKGROUND OF THE INVENTION

This invention relates to liposomal formulations of compounds such as drugs. More particularly this invention relates to methods of encapsulating anesthetics in multivesicular liposomes with high efficiency and sustained in vivo rates of release.

A local anesthetic's duration of action following administration is usually sufficiently long to cover the pain inflicted during most surgical procedures. However, the duration of action is not long enough to cover most post-operative pain, or pain from many invasive diagnostic procedures, or from injuries. Continuous infusion or repeated infiltration of a local anesthetic into a surgical wound, diagnostic "port" or injury site is impractical. Therefore, a sustained-release formulation of a local anesthetic would be useful for pain management, especially in view of the current trend for out-patient surgeries and emergency care centers. Desirably, such formulations are useful in trauma and diagnostic pain, as well.

Several approaches to develop sustained-release formulations of local anesthetics have been described in the literature. For example, polylactic-co-glycolic acid polymer microspheres containing both bupivacaine and dexamethasone have produced long duration of local anesthesia. Crystalline forms of local anesthetics have also been shown to have long duration of action. Lipophilic bupivacaine free-base incorporated into the membranes of multilamellar liposomes and proton-gradient-loaded large unilamellar liposomes have shown efficacy lasting 6 to 11 hours.

Multivesicular liposomes (MVL) are being developed as a lipid-based sustained-release drug delivery system for local, regional or systemic drug delivery. Sustained release of many water-stable drugs encapsulated into MVL has been shown in animal models via intrathecal, subcutaneous, intraperitoneal and epidural routes of administration, as well as in human patients via intracerebroventricular, intrathecal, subcutaneous and epidural routes. A multicenter, randomized phase III clinical trial of a MVL formulation of cytotoxic agent cytarabine has shown that this formulation is more efficacious than free cytarabine in treating leptomengial carcinoma.

MVL are defined as liposomes containing multiple non-concentric chambers within each liposome particle, resembling a "foam-like" matrix. Such particles are to be distinguished from multilamellar vesicles (MLV), also known as a multilamellar liposome, which contain multiple concentric chambers within each liposome particle. A further distinct particle is the unilamellar vesicle (ULV), also known as a unilamellar liposome, which encloses a single internal aqueous compartment. The present invention relates to MVL. The prior art describes the preparation of MVL (Kim et al., *Biochim. Biophys. Acta* 728, 339-348, 1983).

Many of the cationic biologically active substances used in MVL encapsulation techniques are used as salts of monoprotic mineral acids (for example, as hydrochloride salts). The prior art has used such commonly available monoprotic mineral acid salts of cationic biologically active substances for encapsulation into liposomes without any modification into a salt of diprotic or triprotic mineral acid. The prior art has also used organic acids such as citric or glutamic acids to effect encapsulation.

SUMMARY OF THE INVENTION

The invention provides local anesthetics encapsulated in multivesicular liposomes (MVL), that is, lipid vesicles having multiple non-concentric internal aqueous chambers having internal membranes distributed as a network throughout the MVL. The chambers contain acids which are effective to enable the encapsulation of certain anesthetics and to modulate the release rate of the encapsulated anesthetics. The invention also provides methods of making such compositions, and of providing local anesthesia to subjects by administering the compositions.

The prior art has used commonly available monoprotic (for example, hydrochloride or glutamic) salts of biologically active compounds. This has resulted in either unacceptable formulations for encapsulating the biologically active substances in MVL or very low encapsulation efficiency. The invention results from the surprising finding that inclusion of the free base form of anesthetic compounds solublized with phosphoric acid, or conversion of the commonly available hydrochloride salts of anesthetic compounds into phosphate (salt of triprotic mineral acid) or sulfate salts (salt of diprotic mineral acid) for inclusion into MVL results in markedly improved encapsulation efficiency as well as sustained release in biologically relevant media. Polyalcoholic organic acids such as glucuronic or gluconic acid are also included, wherein such acid is co-encapsulated with anesthetics to assist encapsulation and to effect sustained-release of the anesthetic. Surprisingly, polyalcoholic organic acids are superior to non-polyalcoholic organic acids, giving compositions with high encapsulation efficiency and sustained release of anesthetic. Polyalcoholic organic acids greatly improve the encapsulation of anesthetic and the acceptability of the formulation. Sulfate salts and a number of other salts require the inclusion of such acids to form acceptable formulations.

When the encapsulated anesthetic is administered as a single intracutaneous or subcutaneous dose, the duration of anesthesia and half-life of the drug at the local injection site is increased as compared to injection of unencapsulated anesthetic. The maximum tolerated dose of the encapsulated anesthetic is also markedly increased in the liposomal formulation over injection of unencapsulated anesthetic.

The major use for the invention is for making sustained-release formulations of biologically active substances that have high diffusion rates through bilayer lipid membranes. Both the use of diprotic and triprotic mineral acid salts of biologically active substances and con-encapsulation of polyalcoholic organic acids enable these difficult-to-encapsulate drugs to be encapsulated easily and released slowly.

Other features and advantages of the invention will be apparent from the following detailed description, and from the claims.

DETAILED DESCRIPTION

Figures 1A, 1B:
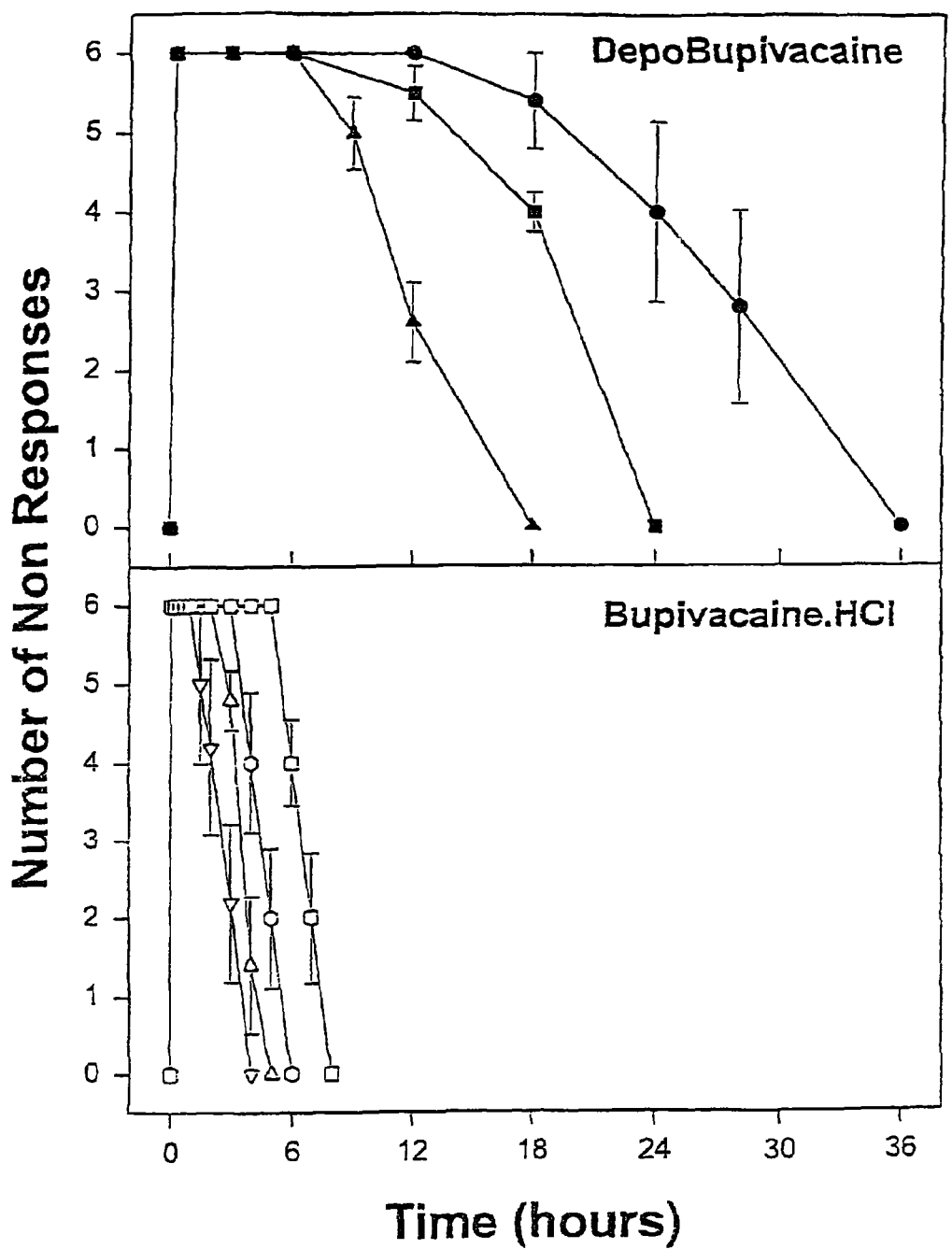
FIG. 1A is a graph showing the anesthetic effect (number of non responses to six pin-pricks) as a function of time following a single intracutaneous dose of MVL-encapsulated bupivacaine phosphate containing different concentrations of bupivacaine.
FIG. 1B is a graph showing the anesthetic effect (number of non responses to six pin-pricks) as a function of time following a single intracutaneous dose of unencapsulated bupivacaine hydrochloride at different concentrations.

Post-operative or post-trauma pain is thought to be most intense in the immediate post-operative or post-injury and subsequent 24-hour period. It is possible that improved control of post-operative pain can decrease pulmonary and gastrointestinal complications and perhaps shorten hospital stay. Systemic opiates commonly used to control pain during this post-operative period can depress pulmonary function and slow gastro-intestinal recovery. Other antinociceptive agents such as non-steroidal anti-inflammatory agent ketorolac tromethamine can increase bleeding and gastrointestinal irritation in this time of stress. Since nociceptive stimuli arising from surgical interventions or traumatic injury are usually local or regional in origin, prolonged local or regional sensory block for pain control is an intriguing concept. Thus, it is believed that improved treatment with local anesthetics involves maintenance of anesthetic level for a prolonged period. Unfortunately, the half-life of many anesthetics is very short after an intraperitoneal (IP), intravenous (IV), intrathecal (IT), intraartricular (IA), intramuscular (IM), or subcutaneous (SC) dose. Therefore, a slow-release preparation which provides a prolonged and sustained exposure at a therapeutic concentration of a local anesthetic is needed. The present invention is directed to the production, composition, and use of such a preparation.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Anesthetics

The present invention provides prolonged release of local anesthetics, particularly of the "amide-type" anesthetics, from MVL following administration of compositions containing the MVL. The invention utilizes a local anesthetic encapsulated in MVL. The local anesthetic generally belongs to the class known as the amide-type anesthetics. The name comes from the presence of the amide (—NHCO—) linkage in the central portion of the molecule. The group linked to the nitrogen end of the amide is a substituted phenyl ring, especially a phenyl ring containing at least one short chain alkyl group, such as methyl, ethyl, propyl or butyl. Examples of such groups include 2-methylphenyl, 2,6-dimethylphenyl, 2-ethylphenyl, 2,6-diethylphenyl, and 2-ethyl-6-methylphenyl. If the substituent group is 2,6-dimethylphenyl, the local anesthetics are also referred to as 2,6-xylidide anesthetics.

The group linked to the CO end of the amide linkage is designated as $CHR_1R_2$. In the foregoing designation, $R_1$ is a secondary or tertiary alkyl amine such as N-alkyl amine or N,N-dialkyl amine. Short chain alkyl groups (from one to four carbon atoms) are preferred. Examples include N-methyl amine, N-ethylamine, N-propylamine, N-butylamine, N,N-dimethylamine, N,N-diethylamine, N-ethyl-N-methylamine, and similarly constructed substituents. The three and four member alkyl chains can be of any configuration, that is, straight chain (n-alkyl), or branched (iso-, sec-, or tert-alkyl). Alternatively, $R_1$ can be a secondary or tertiary alkyleneamino group, which further links to $R_2$. For example, $R_1$ and $R_2$ can be linked by a secondary or tertiary nitrogen-containing alkyl chain, to form an N-alkyl substituted piperidine or pyrrolidine ring. In such examples, the N-alkyl group is preferably a short chain (one to four carbon atoms), such as N-methyl, N-ethyl, N-propyl or N-butyl, in which the chain can be straight or branched. The $R_1$-$R_2$ linking substituent can be 2-piperidyl, 2-pyrrolidyl, 3-piperidyl, 3-pyrrolidyl, 4-piperidyl or 4-pyrrolidyl. Preferably, the substituent formed when R1 and R2 are linked by a secondary or tertiary nitrogen-containing alkylene chain is 2-piperidyl or 2-pyrrolidyl. The stereochemistry of the compounds can be either R or S, depending on the most efficient anesthetic activity. For example, commercially available ropivacaine is found in the (S)(-) configuration. Bupivicaine is also found in the form known as levo-bupivacaine. In the foregoing designation, $R_2$ is either hydrogen, short chain alkyl (one to four carbon atoms) or a secondary or tertiary alkyleneamino chain which links to $R_1$, as described above.

The amide-type anesthetics which are useful in the present invention are described by the following structure:

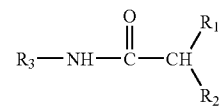

wherein $R_1$, and $R_2$ are as described above, and $R_3$ is an alkyl-substituted phenyl ring, as described above.

Illustrative of the forgoing description of the amide-type anesthetics useful in the present invention are, for example, bupivacaine, levo-bupivacaine, mepivacaine, lidocaine, pyrrocaine, prilocaine, and ropivacaine.

The anesthetics should be present in the compositions of the invention in concentrations of from about 0.01% to about 5.0% w/v, or preferably from about 0.5% to about 2.0% w/v. The weight percentages are defined as weight of anesthetic per volume of MVL.

The free base forms of local anesthetics of the invention can be solublized. Desirably, the water-soluble salt form is formed for their storage and delivery from MVL. The salt form can be introduced to the first aqueous phase of the MVL as such, or can be formed by adding the free base form, and sufficient acid to solublize the anesthetics to the desired extent. The salt can be any pharmaceutically acceptable di- or tri-protic mineral salt, such as the phosphate or sulfate salt.

Also useful are the polyhydroxyl carboxylic acid salts of the anesthetic, such as the tartarate, gluconate or gluconurate salts. Combinations of such salts are preferable as components of the first aqueous phase of the inventive compositions. Thus, amide-type anesthetics are present in the pharmaceutical compositions of the invention in the form of polyhydroxy carboxylate salts, and di- and tri-protic mineral salts. Preferred embodiments of the invention are those with a binary mixture of amide-type anesthetic salts, one derived from a polyhydroxy carboxylic acid, and the other derived from a di- or tri-protic mineral acid.

Multivesicular Liposomes

The anesthetic compositions of the invention also include multivesicular liposomes (MVL) which encapsulate and provide modulated and sustained release of the anesthetics described above. The MVL are made by the following process. A "water-in-oil" type emulsion containing a non-hydrohalic acid salt of any of the anesthetics described above is formed from two immiscible phases, a lipid phase and a first aqueous phase.

The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholine, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamine.

Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

Many types of volatile organic solvents can be used in the present invention, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the anesthetic compositions of the present invention.

Optionally, but highly desirably, other components are included in the lipid phase. Among these are cholesterol or plant sterols.

The first aqueous phase includes an anesthetic, at least one polyhydroxy carboxylic acid, and at least one di- or tri-protic mineral acid. In some embodiments of the invention, also included is hydrochloric acid. Hydrochloric acid is not an essential constituent, but rather is optional and desirable in some embodiments. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled strictures or porous pipes, by ultrasound, or by nozzle atomization, to produce a water-in-oil emulsion. Thus, the anesthetics of the invention are encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the anesthetic dissolved therein. The second aqueous phase can contain additional components such as glucose, and/or lysine.

The volatile organic solvent is then removed from the spherules, for instance by surface evaporation from the suspension. When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

Method of Providing Anesthesia

The invention also provides a method of providing regional aesthesia to a subject by administering the claimed anesthetic compositions either intracutaneously, subcutaneously or via a local or regional nerve block. The dosages can be administered either as a nerve block (including to the limit of acting as a motor block), or as a sensory block.

The term "therapeutically effective" as it pertains to the compositions of this invention means that an anesthetic present in the first aqueous phase within the MVL is released in a manner sufficient to achieve a particular level of anesthesia. Exact dosages will vary depending on such factors as the particular anesthetic, as well as patient factors such as age, sex, general condition, and the like. Those of skill in the art can readily take these factors into account and use them to establish effective therapeutic concentrations without resort to undue experimentation.

Generally however, the dosage range appropriate for human use includes the range of from about 20 mg to about 300 mg of total anesthetic. The upper limit is limited by the toxicity of the particular anesthetic, and the lower limit is approximately 10% of the upper limit.

The invention will be further described in the following examples, which do not limit the scope of the invention described in the claims.

EXAMPLES

The following examples illustrate the preparation and properties of certain embodiments of the present invention.

Example 1

Manufacture of Bupivacaine-phosphate-containing MVL

Bupivacaine hydrochloride (Sigma Chemical Co., St. Louis, Mo.) was converted into bupivacaine phosphate by initial precipitation of aqueous bupivacaine hydrochloride with 1N sodium hydroxide to prepare the free base. The precipitate was extensively washed with water, and then converted into phosphate salt with an equimolar amount of phosphoric acid. For each batch of the formulation, 5 mL of a discontinuous first aqueous component containing 60 mg/mL of bupivacaine phosphate, 150 mM glucuronic acid, 15 mN hydrochloric acid, and 20 mM phosphoric acid was added to a mixer vessel containing a lipid component containing 5 mL of USP chloroform (Spectrum Chemical Co., Gardena, Calif.) as solvent, and 18.6 mM 1,2-dierucoyl-sn-glycero-3-phosphocholine (DEPC), 4.2 mM dipalmitoyl phosphatidylglycerol (Avanti Polar-Lipids, Inc., Alabaster, Ala.) (an anionic amphipathic lipid), 30 mM cholesterol (Avanti Lipids), and 10.8 mM tricaprylin. The immiscible first aqueous component and lipid component were mixed at 16,000 rpm in an Omni-mixer (OMNI International, Gainesville, Va.) for 9 minutes. The resulting water-in-oil emulsion was transferred to a 50 mL mixing vessel containing 25 mL of a continuous second aqueous component containing 32 mg/mL of glucose and 10 mM free-base lysine (Sigma Chemical Co., St. Louis, Mo.). The mixture was then mixed for 20 seconds at 4000 rpm in an Omni mixer.

The resulting water-in-oil-in-water double emulsion was transferred to a 1 L Erlenmeyer flask containing 275 mL of the continuous second aqueous phase (glucose, 32 mg/mL; free-base lysine, 40 mM). The chloroform was evaporated for 15 minutes under a constant flow (90 L/min) of nitrogen gas at 37° C. to form MVL particles in suspension. The MVL particles were isolated by centrifugation at 200×g for 10 minutes, then washed three times with a 0.9 percent (w/v) solution of NaCl. Each batch was stored at 2-8° C. and used for subsequent studies within 48 hours.

Example 2

Recovery of Bupivicaine from Different MVL Formulations

The bupivicaine samples were soublized by adding an equimolar volume of a 1M solution of the indicated acid and then slowly adding, with stirring, additional water until 60 mg/mL or a clear solution was achieved. The pH was then adjusted to approximately 5. The final bupivicaine concentration was determined by HPLC against an internal standard.

For each formulation attempt, the first aqueous phase solution contained the bupivicaine counterion at 60 mg bupivicaine per mL, or the limit of solubility of the bupivicaine counterion, at pH 5. Other parameters for MVL manufacture was as described above. Recovery refers to percent of bupivicaine in counterion solution encapsulated and recovered in final MVL product. For study 2, the first aqueous phase also contained 150 mM glucuronic acid. The results are shown in Table 1.

TABLE 1

Recovery of MVL-encapsulated bupivacaine from Formulations Containing Various Acids

| Bupivicaine (mg/mL) | acid included | additional acid | recovery (%) |
|---|---|---|---|
| Study 1 | | | |
| 60 | phosphoric | — | 5.7 |
| 60 | sulfuric | — | (clumped) |
| 23 | nitric | — | no MVL formed |
| 40 | hydrochloric | — | no MVL formed |
| 26 | glucuronic | — | 34 |
| 60 | tartaric | — | clumped |
| 41 | acetic | — | no MVL formed |
| 2.2 | perchloric | — | no MVL formed |
| Study 2 | | | |
| 60 | phosphoric | 150 mM glucuronic | 35 |
| 60 | sulfuric | 150 mM glucuronic | 16 |
| 23 | nitric | 150 mM glucuronic | 45 |
| 40 | hydrochloric | 150 mM glucuronic | 16 |
| 26 | glucuronic | 150 mM glucuronic | 48 |
| 60 | tartaric | 150 mM glucuronic | 20 |
| 41 | acetic | 150 mM glucuronic | 18 |
| 2.2 | perchloric | 150 mM glucuronic | no MVL formed |
| 60 | citric | 150 mM glucuronic | 13 |
| 60 | malic | 150 mM glucuronic | 19 |
| 60 | succinic | 150 mM glucuronic | 20 |

The results in Table 1 demonstrate clearly that the addition of a polyhydroxy organic acid (in this case, glucuronic acid) in addition to one of a number of other acids, including triprotic mineral acids such as phosphoric acid, or polyhydroxy organic acids such as glucuronic acid provides a remarkable synergistic effect. This surprising discovery leads to higher loading and recovery of the MVL of the invention than previously found.

Example 3

In vivo Animal Studies using Intracutaneous Injections

Male guinea pigs weighing 800-1000 grams (Harlan Sprague-Dawley, San Diego, Calif.) were used for efficacy studies. Male guinea pigs (Harlan-Sprague-Dawley) weighing 400-600 grams were used for pharmacokinetic studies. The animals were housed, 1 per cage, in a temperature-controlled environment with alternating 12-hour periods of light and darkness and given unrestricted access to food and water. Prior to each study, animals were habituated to the environment for at least 7 days. Female CD 1 mice (Sprague-Dawley) weighing 22-28 grams were used for determination of maximum tolerated dose (MTD) All animals were maintained in accordance with guidelines of the Committee on Care and Use of Laboratory Animals of the Institute of Laboratory Animal Resources, National Research Council.

The formulations of MVL-encapsulated bupivacaine and bupivacaine hydrochloride prepared as described above were diluted in normal saline so that a constant volume of 1 mL contained a dose at concentrations of 2.1%, 1.0%, or 0.5% (w/v) bupivacaine. Concentrations were confirmed by solubilizing a 50 µl aliquot of the MVL formulation in 1 mL of isopropyl alcohol followed by dilution in water and assay by a previously published HPLC method as described (P. Le Guevello et al., *J. Chromatography* 622:284-290, 1993). The HPLC analysis of the MVL formulations revealed that less than 5% of total bupivacaine was present in the formulation as unencapsulated bupivacaine.

Infiltration anesthesia studies were performed in the test guinea pigs using a modified intracutaneous wheal pin-prick model as described (R. H. de Jong et al, *Anesth. Analog* 59:401-5, 1980). On the day preceding the experiment, hairs on the backs of the animals were clipped. Each animal received either a dose of MVL-encapsulated bupivacaine (concentrations of 0.5, 1.0 or 2.1 percent (w/v) bupivacaine) or unencapsulated bupivacaine (concentrations of 0.25, 0.5, 0.75 or 1.0 (w/v) percent bupivacaine), which created a wheal. The margin of the wheal was marked with indelible ink. The reaction to pin pricks at the site of injection was tested just prior to injection (time zero) and 15 minutes, 3, 6, 12, 18, 24, 30 and 36 hours following injection of MVL-encapsulated bupivacaine, and zero, 5, 15, minutes, 1, 1.5, 2, 3, 4, 5, 6, 7 and 8 hours following injection of bupivacaine hydrochloride. The pin pricks were applied first to a control area outside the wheal at each time point. After observing the animal's normal reaction to the pin prick (vocalization response), six pricks were applied inside the wheal and the number of pricks to which the guinea-pig failed to react were recorded as non-responses. Each prick was applied at an interval of 3-5 sec. All animals responded with vocalization to all six pin pricks at baseline.

The animal data obtained indicate a rapid onset of anesthesia following a single intracutaneous dose of bupivacaine encapsulated in MVL, followed by a prolonged duration of sensory anesthesia lasting up to 28 hours, depending on the concentration of bupivacaine in the MVL administered. The rapid onset of anesthesia is attributable, in part, to a low, but a significant fraction of unencapsulated bupivacaine (approximately 5 % of the total) in the batches of MVL encapsulating bupivacaine used in these experiments. The duration of anesthesia obtained by use of these formulations may cover the worst post-operative period, the first 24 hours. A longer anesthesia duration, perhaps 7 days or longer, would be more suitable for chronic pain, such as cancer or neuropathic pain.

Example 4

Data Analysis of Efficacy Studies

Anesthetic efficacy curves were plotted as the number of non-responses as a function of time. Areas under the curve (AUC) were calculated by the trapezoidal rule to the last data point. With regard to FIG. 1A, the MVL-encapsulated bupivacaine concentrations by weight per volume percent (w/v %) were 2.1% (●), 1.0% (■), and 0.5% (▲). With regard to FIG. 1B, unencapsulated bupivacaine concentrations by weight per volume percent were 0.25% (▽), 0.5% (△), 0.75% (◊), and 1.0% (□). Each data point represents the average for 5 to 6 animals. The error bars represent the standard error of mean (SEM).

Evaluation of response to pin pricks showed that complete local anesthesia (no response condition) was achieved within 15 minutes following intracutaneous administration of either the MVL formulation of bupivacaine (FIG. 1A) or of unencapsulated bupivacaine hydrochloride (FIG. 1B).

Figure 2:
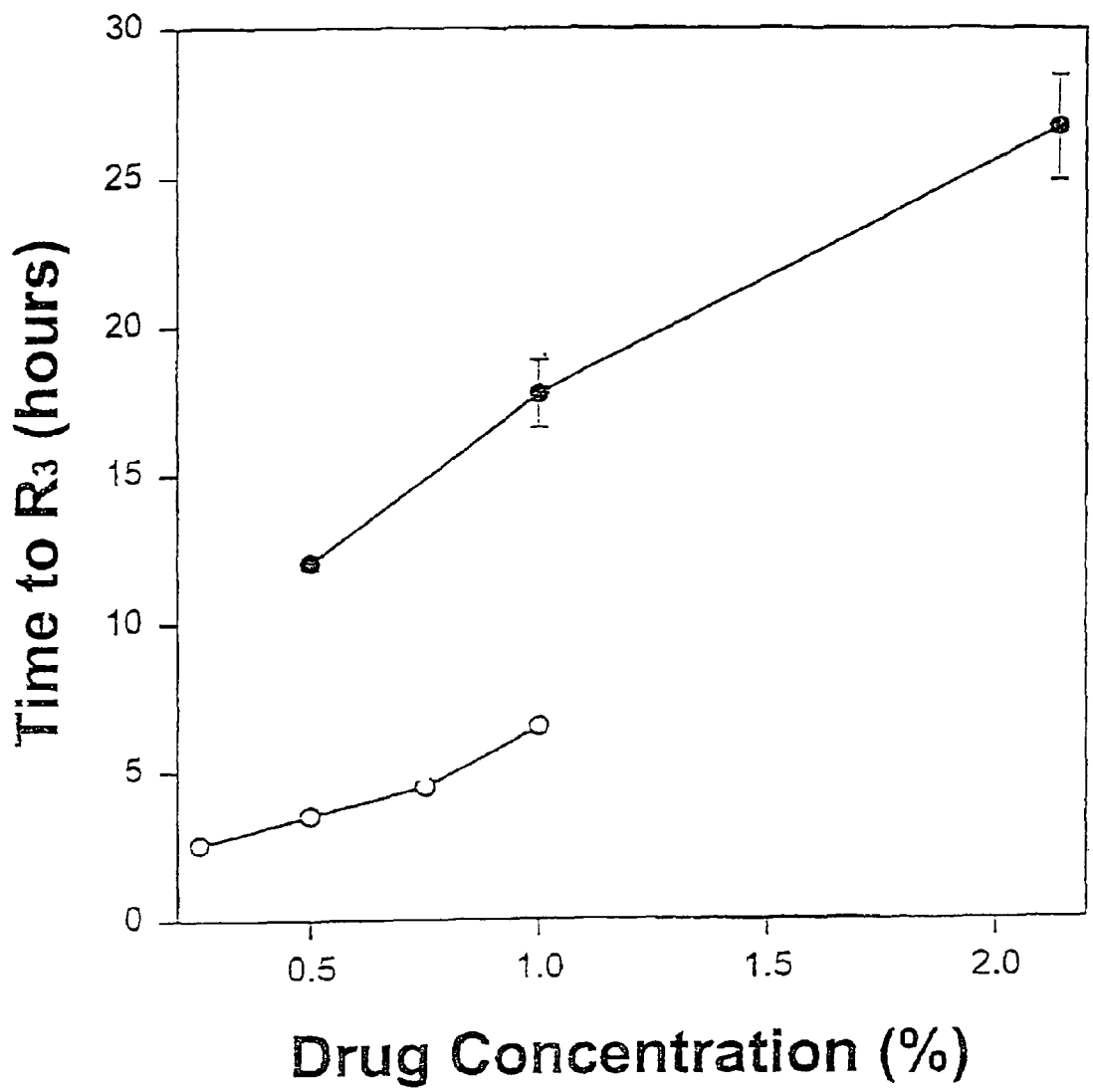
FIG. 2 is a graph showing a comparison of the duration of anesthesia for the formulations of FIGS. 1A (MVL-encapsulated bupivacaine phosphate, filled circles) and 1B (unencapsulated bupivacaine hydrochloride, open circles) as quantified by "time to half maximal response ($R_3$)" (ordinate) versus concentration of administered dose (abscissa).

FIG. 2 shows the duration of anesthetic effect as measured by the time to half maximal response ($R_3$) for the various doses of the MVL formulation (filled circles) and for unencapsulated drug (open circles). Each data point represents the average and standard error of mean (SEM) from 5 to 6 animals. These results show that the duration of anesthetic effect was concentration dependent in both cases. However, the MVL formulations containing concentrations 0.5 and 1.0 percent by weight of bupivacaine phosphate were prolonged 3.2 and 2.9-fold, respectively, as compared to comparable doses of bupivacaine hydrochloride.

Example 5

Determination of Maximum Tolerated Dose (MTD)

Determination of maximum tolerated dose (MTD) was done in mice using a subcutaneous test known in the art (R. H. de Jong et al., *Anesthesiology* 54:177-81, 1981). Groups of three mice each were given injections of either 780 or 980 mg per kg body weight of the above-described MVL formulation containing bupivacaine sulfate as two divided doses of 500 µl each (total 1.0 mL volume). The doses were administered in rapid sequence into each flank. Control groups of 3 mice each received one of the test doses as a single dose of 10, 20, 30 or 50 mg/kg body weight of unencapsulated bupivacaine hydrochloride. MTD was defined as the highest dose at which none of the animals experienced systemic toxicity.

These studies showed that none of the mice that received free bupivacaine hydrochloride subcutaneously showed any signs of systemic toxicity at doses of 10 and 20 mg/kg. However, at 30 and 50 mg/kg doses, two out of three, and three out of three animals, respectively, developed toxicity. On the other hand, the MVL formulation of bupivacaine sulfate administered subcutaneously at a dose of 780 mg/kg showed no sign of systemic toxicity in any of the animals; whereas three out of three animals had toxicity at a dose of 980 mg/kg. Therefore, the MTD for unencapsulated bupivacaine hydrochloride was estimated to be about 20 mg/kg of body weight, and that for MVL-encapsulated bupivacaine sulfate was estimated at about 780 mg/kg of body weight.

The most serious toxicity arising from the use of local anesthetics is seizure or cardiovascular collapse. Consistent with the lower peak serum concentration found following administration of the MVL formulations of bupivacaine, the maximum tolerated dose for the MVL-encapsulated bupivacaine was many times higher than that for bupivacaine hydrochloride. These data would predict an increased systemic safety profile for the compositions produced by the method of this invention. The toxicity profiles of the active and inactive ingredients are well-defined, reducing the likelihood of finding unexpected toxicity.

Example 6

Pharmacokinetic Studies

The in vivo pharmacokinetics of the MVL formulations of bupivacaine and free bupivacaine hydrochloride were compared following a single 1 mL intracutaneous dose of the MVL formulation containing 1.0 percent (w/v) of bupivacaine, or a dose of 0.5 percent (w/v) of unencapsulated bupivacaine hydrochloride to a group of guinea pigs. The lower concentration was selected for bupivacaine hydrochloride because the 400-600 gram animals were unable to tolerate a 1.0% concentration dose of the unencapsulated drug. For the animals that received free bupivacaine hydrochloride, samples were collected at 0 and 30 minutes, and 1, 3, 6, and 9 hours following injection, while the animals that received the MVL formulations of bupivacaine were sampled 0, 6, 12, 18, 24, 48, and 72 hours following injection. At each time point, 3 or more animals were first anesthetized with halothane and then exanguinated by cardiac puncture. Serum samples were obtained by centrifugation of clotted whole blood. Skin was collected around the injection site with 3 cm margins, together with a 2-3 mm layer of underlying subcutaneous tissue. The skin and serum samples were kept frozen at −20° C. until analysis.

The amount of total bupivacaine remaining in the injection site was obtained by mincing the tissue followed by in toto homogenization in water using a Polytron homogenizer, (Brinkman, Littau, Switzerland). Bupivacaine was extracted from the homogenate and analyzed by HPLC using a previously published method (Le Guevello et al., *J. Chromatography* 622:284-290, 1993). Bupivacaine concentration in serum was determined by extraction followed by HPLC (Le Guevello et al., supra). Tetracaine spiked into each sample before extraction was used as an internal standard. The limit of detection of the assay was 20 ng/mL.

Pharmacokinetic data obtained from the samples were analyzed using a noncompartmental model (WinNonlin software, Scientific Consulting, Inc., Apex, N.C.). Parameters calculated were the drug amount remaining at the injection site, the area under the "amount vs. time" curve (AUC), and drug half-life ($t_{1/2}$). In addition to the AUC and half-life, peak concentration ($C_{max}$) was also reported for serum bupivacaine pharmacokinetics.

One way analysis of variance (ANOVA) was used to separately determine dose dependency for the different drug formulations and route of administration (via MVL or free drug) as well as for comparison between formulations. Student-Newman-Keuls tests were used on all ANOVA analyses. The pharmacokinetic parameters obtained by these methods are summarized in Table 2 below.

TABLE 2

Pharmacokinetic Parameters Following Either a Single 1.0% DepoBupivacaine or 0.5% Bupivacaine Hydrochloride Intracutaneous Injection

|  | MVL-encapsulated Bupivacaine | Bupivacaine hydrochloride |
|---|---|---|
| Drug Concentration Administered | 1.0% | 0.5% |
| Peak Amount (mg), Skin | 11.6 | 3.8 |
| $t_{1/2}$ (hr), Skin | 12.0 | 1.3 |
| AUC (mg * hr), Skin | 236 | 2.9 |
| $C_{max}$ (µg/mL), Serum | 2.9 | 6.5 |
| $t_{1/2}$ (hr), Serum | 20.5 | 2.1 |
| AUC (µg * hr * mL$^{-1}$), Serum | 56.1 | 21.2 |
| $r^2$, Skin | 0.97 | 0.85 |
| $r^2$, Serum | 0.89 | 0.93 |

The "drug concentration administered" is in units of weight of anesthetic per volume of MVL. The "peak amount" shows the maximum amount of the indicated substance in the skin sample. The "Cmax" is the maximum concentration of the indicated substance in serum. The "$t_{1/2}$" is the drug half-life. The "AUC area" is the area under the "amount vs. time" curve. The "$r^2$" is the square of the sample correlation coefficient.

As these results show, following intracutaneous administration of the MVL formulation, the total amount of drug in the injection-site tissue decreased with a half-life of 12 hours compared to 1.3 hours for unencapsulated bupivacaine hydrochloride. Peak serum concentration of bupivacaine following a single intracutaneous dose of the 1.0% MVL formulation was decreased 2.2 fold (4.4 fold when corrected for the dose) compared to that following 0.5% bupivacaine hydrochloride. Similarly, the terminal serum half-life for 1.0 percent (w/v) MVL formulations was 20.5 hours compared to 2.1 hours for unencapsulated bupivacaine hydrochloride at a concentration of 0.5 percent (w/v).

The local injection site AUC for the MVL formulation was 81 times (41 times when corrected for the dose) that for unencapsulated bupivacaine hydrochloride, and the serum AUC was 2.6 times (1.3 times when corrected for the dose) that for bupivacaine hydrochloride.

Figures 3A, 3B:
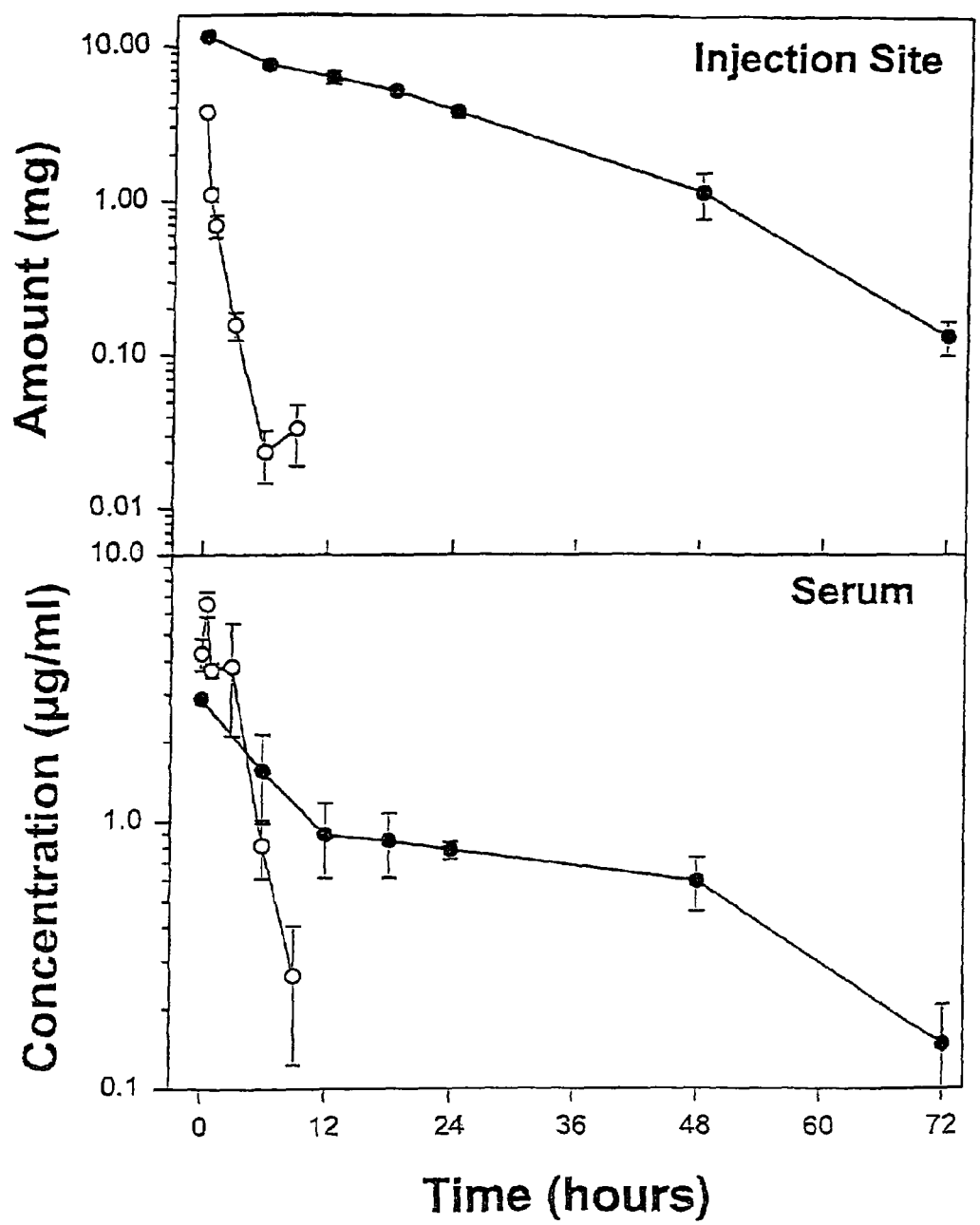
FIG. 3A is a graph showing the total amount of bupivacaine (mg) remaining at an injection site Up to 72 hours following a single intracutaneous dose of MVL-encapsulated bupivacaine phosphate (filled circles) or unencapsulated bupivacaine hydrochloride (open circles).
FIG. 3B is a graph showing the serum bupivacaine concentrations (μg/mL) up to 72 hours following a single intracutaneous dose of MVL-encapsulated bupivacaine phosphate at a concentration of 1.0 percent (w/v) of bupivacaine (filled circles) or 0.5 percent (w/v) of unencapsulated bupivacaine hydrochloride (open circles).

FIGS. 3A and 3B show the result of the pharmacokinetic studies. FIG. 3A shows the amount of either MVL-encapsulated bupivacaine at a concentration of 1.0 percent (w/v) of bupivacaine (filled circles) or unencapsulated bupivacaine hydrochloride at a concentration of 0.5 percent (w/v) of bupivacaine (open circles) remaining at an injection site at time points tested over a period of 72 hours. FIG. 3B shows the serum concentration (µg/mL) of bupivacaine following a single intracutaneous dose of the MVL-encapsulated formulation at 1.0 percent (w/v) of bupivacaine (filled circles) or unencapsulated bupivacaine hydrochloride at a concentration of 0.5 percent (w/v) of bupivacaine (open circles). Each data point represents the average and standard error of mean (SEM) from 3 to 6 animals. A statistical significance level of 0.05 was used for all tests.

The pharmacokinetics data obtained in the Examples herein were consistent with a prolonged duration of anesthetic effect. The anesthesia duration was 2.9- to 3.2-fold longer for bupivacaine encapsulated in MVL, and the half-life at the injection site was 9.2-fold longer compared to bupivacaine hydrochloride. The peak serum concentration was decreased by 4.5 fold (normalized to equivalent doses), and the terminal serum half-life was increased by 9.8-fold following administration of bupivacaine encapsulated in MVL compared to bupivacaine hydrochloride.

In conclusion, a single intracutaneous dose of bupivacaine encapsulated in MVL resulted in a prolonged duration of anesthesia (up to 28 hours) and a 9.2-fold (uncorrected for dose) increase in local injection-site half-life compared to bupivacaine hydrochloride. The maximum tolerated dose was increased by 39 fold compared to bupivacaine hydrochloride. Therefore the formulations of the invention have utility for sustained infiltration anesthesia without the need for continuous infusion and may increase patient satisfaction.

A number of embodiments of the present invention have been described. Nevertheless, it will be understood that various aspects, advantages and modifications of the invention may be made without departing from the spirit and scope of the invention. The foregoing description is intended to illustrate and not limit the scope of the invention, which is defined by the scope of the appended claims.

We claim:

1. A multivesicular liposome formulation comprising bupivacaine phosphate made by a process comprising:
   a) preparing a first aqueous component comprising at least one acid in sufficient quantity to solubilize bupivacaine or a salt thereof, said acid being phosphoric acid;
   b) preparing a lipid component comprising at least one organic solvent, at least one amphipathic lipid, and at least one neutral lipid lacking a hydrophilic head group;
   c) mixing said first aqueous component and said lipid component to form a water-in-oil emulsion, wherein at least one component comprises bupivacaine or a salt thereof;
   d) mixing said water-in-oil emulsion with a second aqueous component to form solvent spherules; and
   e) removing the organic solvent from the solvent spherules to form multivesicular liposomes.

2. The multivesicular liposome formulation made by a process of claim 1, wherein said amphipathic lipid is dierucoylphosphatidyl choline.

3. The multivesicular liposome formulation made by a process of claim 1, wherein said amphipathic lipid is dipalmitoylphosphatidyl glycerol.

4. The multivesicular liposome formulation made by a process of claim 1, wherein said neutral lipid is tricaprylin.

5. A pharmaceutical composition comprising multivesicular liposomes encapsulating bupivacaine phosphate, said multivesicular liposome comprising
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposome encapsulating bupivacaine is made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to provide multivesicular liposomes encapsulating bupivacaine phosphate.

6. The pharmaceutical composition made by a process of claim 5, wherein said at least one amphipathic lipid is selected from the group consisting of dierucoylphosphatidylcholine and dipalmitoylphosphatidylglyceral.

7. The pharmaceutical composition made by a process of claim 5, wherein said at least one amphipathic lipid comprises dierucoylphosphatidylcholine.

8. The pharmaceutical composition made by a process of claim 5, wherein said at least one amphipathic lipid comprises dipalmitoylphosphatidylglycerol.

9. The pharmaceutical composition made by a process of claim 5, wherein said at least one neutral lipid comprises tricaprylin.

10. The pharmaceutical composition made by a process of claim 5, wherein said at least one amphipathic lipid comprises dierucoylphosphatidylcholine and/or dipalmitoylphosphatidyl glycerol, and said at least one neutral lipid comprises tricaprylin.

11. The pharmaceutical composition made by a process of claim 5, wherein the amphipathic lipid is dierucoylphosphatidylcholine and dipalmitoylphosphatidyl glycerol; and each neutral lipid is selected from the group consisting of triolein, tripalmitolein, trimyristolein, trilinolein, tributyrin, tricaproin, tricaprylin, and tricaprin.

12. The pharmaceutical composition made by a process of claim 11, wherein the neutral lipid is tricaprylin.

13. The pharmaceutical composition made by a process of claim 12, including cholesterol.

14. A method providing regional anesthesia to a subject in need thereof by administering in a single dose a multivesicular liposome comprising a therapeutically effective amount of bupivacaine phosphate, wherein the multivesicular liposome comprises bupivacaine phosphate; a lipid component comprising at least one amphipathic lipid and at least one neutral lipid lacking a hydrophilic head group; and, optionally, a cholesterol and/or a plant sterol.

15. The method of claim 14, wherein the single dose administration is intracutaneously, subcutaneously, or via nerve block.

16. The method of claim 15, wherein the nerve block is local or regional nerve block.

17. The method of claim 14, wherein the regional anesthesia has a duration of 12 hours or more.

18. A method of treating post-operative or post-trauma pain in a subject in need thereof comprising administering in a single dose a multivesicular liposome comprising a therapeutically effective amount of bupivacaine phosphate, wherein the multivesicular liposome comprises bupivacaine phosphate; a lipid component comprising at least one amphipathic lipid and at least one neutral lipid lacking a hydrophilic head group; and, optionally, a cholesterol and/or a plant sterol.

19. The method of claim 18, wherein the single dose administration of a multivesicular liposome comprising a therapeutically effective amount of bupivacaine phosphate provides pain relief of 12 hours or more.

20. The method of claim 18, wherein the single dose contains from at least 20 mg of bupivacaine present in the phosphate salt form.

21. The method of claim 18, wherein the single dose contains from about 20 mg to about 300 mg of bupivacaine present in the phosphate salt form.

* * * * *